/

US005643943A

United States Patent [19]
Gamache et al.

[11] Patent Number: 5,643,943
[45] Date of Patent: *Jul. 1, 1997

[54] SYSTEMIC ADMINISTRATION OF ESTERS AND AMIDES OF ANTIOXIDANTS WHICH MAY BE USED AS ANTIOXIDANT PRODRUG THERAPY FOR OXIDATIVE AND INFLAMMATORY PATHOGENESIS

[75] Inventors: Daniel A. Gamache; Mark R. Hellberg, both of Arlington; Jon C. Nixon, Mansfield; Gustav Graff, Cleburne, all of Tex.

[73] Assignee: Alcon Laboratories, Inc., Fort Worth, Tex.

[*] Notice: The term of this patent shall not extend beyond the expiration date of Pat. No. 5,607,966.

[21] Appl. No.: 472,445

[22] Filed: Jun. 7, 1995

Related U.S. Application Data

[63] Continuation-in-part of Ser. No. 362,718, Dec. 23, 1994, Pat. No. 5,607,966.

[51] Int. Cl.$^6$ .......................... A61K 31/335; A61K 31/34
[52] U.S. Cl. ..................... 514/456; 514/469; 514/622
[58] Field of Search .................................. 514/456, 464, 514/622

[56] References Cited

FOREIGN PATENT DOCUMENTS

| | | | |
|---|---|---|---|
| 0 387 771 A2 | 9/1990 | European Pat. Off. | ...... C07D 311/72 |
| 0 525 360 A2 | 2/1993 | European Pat. Off. | ...... C07C 235/34 |
| 0 527 458 A1 | 2/1993 | European Pat. Off. | ...... C07C 233/22 |
| 3407 507 A1 | 9/1985 | Germany . | |
| 64-40484 A2 | of 1989 | Japan | ...................... C07D 491/052 |

OTHER PUBLICATIONS

Duniec, Z., et al.; "Antioxidant properties of some chemicals vs their influence on cyclooxygenase and lipoxidase activities", *Biochemical Pharmacology*, vol. 32, No. 14, pp. 2283–2286 (1983).
Bellavite, P.; "The Superoxide–Forming Enzymatic System of Phagocytes", *Free Radical Biology & Medicine*, vol. 4, pp. 225–261 (1988).
Duchstein, H., et al.; "Activated Species of Oxygen: A Challenge to Modern Pharmaceutical Chemistry", *Archives of Pharmacology*, vol. 325, pp. 129–146 (1992).
Sies, H., et al.; "Role of tocopherols in the protection of biological systems against oxidative damage", *Journal of Photochemistry and Photobiology*, vol. 8, pp. 211–224 (1991).
Chow, C.; "Vitamin E and Oxidative Stress", *Free Radical Biology & Medicine*, vol. II, pp. 215–232 (1991).
Petty, M., et al.; "Protective effects of an α-tocopherol analogue against myocardial reperfusion injury in rats", *European Journal of Pharmacology*, vol. 210, pp. 85–90 (1992).
Stampfer, M., et al.; "Vitamin E Consumption and the Risk of Coronary Disease in Women", *New England Journal of Medicine*, vol. 328, No. 20, pp. 1444–1449 (1993).

Steinberg, D., et al.; "Lipoprotein and Atherogenesis", *JAMA*, vol. 264, No. 3, pp. 3047–3052 (1990).
Rimm, E., et al.; "Vitamin E Consumption and the Risk of Coronary Heart Disease in Men", *New England Journal of Medicine*, vol. 328, No. 20, pp. 1450–1456 (1993).
PBJ Publications Ltd., *Scrip*, No. 1574, p. 31 (1990).
Carew, T., et al.; "Antiatherogenic effect of probucol unrelated to its hypocholesterolemic effect: Evidence that antioxidants in vivo can selectively inhibit low density lioprotein degradation in macrphage-rich fatty streaks and slow the progression of atherosclerosis in the Watanabe heritable hyperlipidemic rabbit", *Proceedings of the National Academy of Science, U.S.A.*, vol. 84, pp. 7725–7729 (1987).
Halliwell, et al.; "[1] Role of Free Radicals and Catalytic Metal Ions in Human Disease: An Overview", *Methods in Enzymology*, vol. 186, pp. 1–85 (1990).
Campbell, W.; "Lipid–Derived Autacoids: Eicosanoids and Platelet–Activating Factor", *Goodman and Gilman's The Pharmacological Basis of Therapeutics*, Pergman Press, NY, pp. 600–617 (1990).
Gifford, H.; "On the Treatment of Sympathetic Ophthalmia by Large Doses of Salicylate of Sodium, Aspirin, or Other Salicylic Compounds", *Ophthalmoscope*, vol. 8, pp. 257–259 (1910).
Vane, J., et al.; "Inflammation and the mechanism of action of anti–inflammatory drugs", *FASEB Journal*, vol. 1, pp. 89–96 (1987).
Rainsford, K. D. *Inflammation and Mechanisms and Actions of Traditional Drugs, vol. I Anti–inflammatory and Anti–rheumatic drugs*, Boca Raton, FL, CRC Press (1985).
Insel, P.; "Analgesic–Antipyretics and Antiinflammatory Agents: Drugs Employed in the Treatment of Rheumatoid Arthritis and Gout", *Goodman and Gilman's The Pharmacological Basis of Therapeutics*, pp. 638–669, 681 (1990).
Bonne, C., et al.; "2–(2–Hydroxy–4–methylphenyl)aminothiazole Hydrochloride as a Dual Inhibitor of Cyclooxygenase/Lipoxygenase and a Free Radical Scavenger", *Drug Research*, vol. 39(II), No. 10, pp. 1242–1250 (1989).
Nelson, P.; "Cyclooxygenase Inhibitors", *CRC Handbook of Eicosanoids: Prostaglandins and Related Lipids, vol. II, Drugs Acting Via the Eicosanoids*, CRC Press, Boca Raton, FL., pp. 59–133 (1989).
Cohen, N., et al.; "Lewis Acid Mediated Nucleophilic Substitution Reactions of 2–Alkoxy–3, 4–dihydro–2H–1benzopyrans: Regiochemistry and Utility in the Synthesis of 3,4–Dihydro–2H–1–benzopyran–2–carboxylic Acids", *Journal of Organic Chemistry*, vol. 54, pp. 3282–3292 (1989).

(List continued on next page.)

*Primary Examiner*—Robert Gerstl
*Attorney, Agent, or Firm*—Michael C. Mayo

[57] ABSTRACT

Methods for treating vascular inflammatory pathologies are disclosed. Particularly, the methods utilize pharmaceutical compositions containing certain compounds having an anti-inflammatory and anti-oxidant moiety covalently linked by an amide or ester bond. The compounds are useful in preventing and treating inflammatory disorders through several mechanisms.

16 Claims, No Drawings

OTHER PUBLICATIONS

Lamba, O., et al.; "Spectroscopic detection of lipid peroxidaiton products and structural changes ina sphingomyelin model system", *Biochemica et Biophica Acta,* vol. 1081, pp. 181–187 (1991).

Skoog, W., et al.; "Studies on the Fibrinogen, Dextran and Photohemagglutin in Methods of Isolating Leukocytes", *Blood,* vol. II, pp. 436–454 (1956).

Graff, G., et al.; "1-[4-[3-[4-[Bis(4-Fluorophenyl)Hydroxymethyl]-1-Piperidinyl]Propoxy]-3-Methoxyphenyl]Ethanone(AHR-5333): A Selective Human Blood Neutrophil 5-Lipoxygenase Inhibitor", *Prostaglandins,* vol. 38, pp. 473–496 (1989).

Momsen, W., et al.; "Lipid Structural Reorganization Induced by the Pancreatic Lipase Cofactor, Procolipase", *Biochemistry,* vol. 34, pp. 7271–7281 (1995).

Smaby, J. M., et al; "Characterization of Lipid Miscibility in Liquid-Expanded Monolayers at the Gas–Liquid Interface", *Langmuir,* vol. 8, No. 2, pp. 563–570 (1992).

Bazan, H.; "Response of Inflammatory Lipid Mediators following Corneal Injury", *Lipid Mediators in Eye Inflammation New Trends Lipid Mediators Res.* Basel Karger vol. 5, pp. 1–11 (1990).

Goa, K., et al.; "Ocular Diclofenac", *Drugs & Aging,* vol. 2(6), pp. 473–486 (1992).

SYSTEMIC ADMINISTRATION OF ESTERS AND AMIDES OF ANTIOXIDANTS WHICH MAY BE USED AS ANTIOXIDANT PRODRUG THERAPY FOR OXIDATIVE AND INFLAMMATORY PATHOGENESIS

The present application is a continuation-in-part of U.S. patent application Ser. No. 08/362,718, filed Dec. 23, 1994 now U.S. Pat. No. 5,607,966.

BACKGROUND OF THE INVENTION

The present invention is directed to methods of treating vascular inflammatory pathologies such as atheroslcerosis and stroke. In particular, the invention is directed to the use of certain compounds having potent anti-inflammatory and anti-oxidant activity.

Free radical molecules play a major role in inflammation and other tissue pathology. These unstable chemical moieties cause the oxidation of biomolecules which can result in tissue damage. Such oxidative stress and damage has been described in *Biochemical Pharmacology*, volume 32(14), pages 2283–2286 (1983) and *Free Radicals in Biology and Medicine*, volume 4, pages 225–261 (1988). Agents that act as anti-oxidants can protect against oxidative damage. Such protection has been the subject of numerous scientific publications, including the following:

*Archives of Pharmacology*, volume 325, pages 129–146 (1992);

*Journal of Photochemistry and Photobiology*, volume 8, pages 211–224 (1991);

*Free Radicals in Biology and Medicine*, volume 11, pages 215–232 (1991); and

*European Journal of Pharmacology*, volume 210, pages 85–90 (1992).

Oxidation of various biomolecules in the vasculature has been implicated in numerous cardiovascular pathologies including atherosclerosis, thrombosis, myocardial infarction and congestive heart failure. In particular, several reports demonstrate a correlation between the oxidation of low-density lipoproteins (LDL) and the progression of atherosclerotic lesions (*New England Journal of Medicine*, volume 328(20), pages 1444–1449 (1993)). These oxidized LDLs have been further characterized in several pathological events including: 1) chemotaxis, which draws monocytes to the afflicted tissue; 2) differentiation of monocytes into macrophages; 3) uptake of LDL by macrophages to form foam cells; 4) proliferation of smooth muscle cells; 5) development of atherosclerotic lesions; and 6) cytotoxic effects on endothelial cells as well as increases in arterial vasoconstriction (*JAMA*, volume 264(3), pages3047–3052 (1990)).

The use of antioxidants to ameliorate coronary heart disease has been explored. Epidemiological studies have correlated the dietary intake of Vitamin E with reduced risk to coronary heart disease (*New England Journal of Medicine*, volume 328(20), pages 1444–1449 (1993); and *New England Journal of Medicine*, volume 328 (20), pages 1450–156 (1993)). β-carotene, a naturally occuring anti-oxidant, has been pursued in the clinic for cardiovascular disease indications (Scrip No., 1574:31 (1990)). Additionally, research has shown that treatment of hypercholesterolemic animals with antioxidant drugs, including the phenolic antioxidant compound, probucol, has reduced the development of atherosclerosis (*Proceedings of the National Academy of Science*, U.S.A., volume 84, pages 7725–7729 (1989)).

Oxygen radicals have also been implicated in the pathogenesis of a number of other inflammatory conditions. Such conditions have included stroke, rheumatoid arthritis, retinopathy and endotoxic liver injury. It is believed that antioxidants would be useful in treating such conditions (*Methods in Enzymology*, volume 186, pages 1–85 (1990)).

Inflammation from cellular stress can also cause excessive tissue damage. Numerous biochemical pathways are known to lead to inflammation. In general, the cyclooxygenase system produces prostaglandins, while the lipoxygenase system produces leukotrienes, "HETEs" and "HPETEs." See generally, *Goodman and Gilman's The Pharmacological Basis of Therapeutics*, pages 600–617, Pergman Press, NY (1990). Therapies designed to inhibit the production of these types of agents are therefore of great interest.

Anti-inflammatory therapy has been suggested as an adjuvant to the treatment of various cardiovascular indications. These agents assist in preventing thrombotic and atherosclerotic occlusions and restenosis of the vasculature by inhibiting platelet and leukocyte aggregation. Non-steroidal anti-inflammatory agents (NSAIA) have been used for the treatment of inflammatory disorders. The following references may be referred to for further background concerning this use of NSAIAs:

*Ophthalmoscope*, volume 8, page 257 (1910);

*FASEB Journal*, volume 1, page 89 (1987); and

*Inflammation and Mechanisms and Actions of Traditional Drugs, Vol. I Anti-inflammatory and Anti-rheumatic drugs*. Boca Raton, Fla., CRC Press, (1985).

As such, aspirin has been prescribed broadly, for anti-inflammatory and analgetic indications, as well as for patients with unstable angina. Ibuprofen and naproxen have been prescribed for treatment of rheumatoid arthritis and moderate pain. However, there are some problems associated with NSAIA treatment including delivery to the appropriate site of action and side effects (*Goodman and Gilman's The Pharmacological Basis of Therapeutics*, pages 638–669, Pergroan Press, NY (1990)).

The combination of anti-oxidant activity with other pharmacologically significant activities in a single molecule is discussed in JP 64-40484 and EP 387771 A2; and compounds with cyclooxygenase/5-lipoxygenase and anti-oxidant activity are discussed in *Drug Research*, volume 39(II) number 10, pages 1242–1250 (1989). However, these references do not disclose the compounds of the present invention.

The present invention is directed to methods for the prevention and amelioration of oxidative and/or inflammatory pathologies in mammals. The methods of the present invention utilize compositions containing novel compounds that have both potent anti-inflammatory activity and potent anti-oxidant activity in a single molecule. The use of a single chemical entity with potent anti-inflammatory and potent anti-oxidant activity provides increased protection relative to the use of a compound with singular activity. The use of a single agent having both activities over a combination of two different agents provides uniform delivery of an active molecule, thereby simplifying issues of drug metabolism, toxicity and delivery.

SUMMARY OF INVENTION

The present invention provides methods of using novel compounds having potent anti-inflammatory and anti-oxidant activity for the treatment of vascular diseases such as atherosclerosis and stroke. The dual therapeutic efficacies may act in an additive or synergistic manner to reduce cellular damage. Additionally, the compounds of the present invention also exhibit other anti-inflammatory activity not present in the individual agents.

The compounds of the present invention are useful as cytoprotective agents due to their anti-oxidant activity. These compounds include both a non-steroidal anti-inflammatory agent (NSAIA) moiety and an anti-oxidant moiety. In order to provide effective therapy for inflammatory disorders, the present invention takes advantage of these individual efficacies. In addition, the present invention improves upon these individual efficacies by providing greater drug delivery to the target tissues by means of administering a single drug having multiple therapeutic actions. The present invention also provides compounds that associate with lipid membranes, thus providing bioavailable anti-oxidant protection within lipid molecules susceptible to oxidation. Finally, the compounds of the present invention exhibit therapeutic properties which are not present in the individual moieties of the compounds. These and other advantages of the present invention will be apparent to those skilled in the art based on the following description.

The NSAIA component of the compounds provides anti-inflammatory activity when it is freed from the parent compound. The use of these NSAIAs will provide inhibition of cyclooxygenase, an important enzyme involved in the prostaglandin/inflammafton pathway. The compounds also include an anti-oxidant component. As oxidative stress has been implicated in inflammatory responses, the presence of an anti-oxidant will further help treat the target tissue.

The compounds of the present invention also exhibit intrinsic properties present only in the combined molecule, not in the individual components. One such property is the inhibitory efficacy against 5-lipoxygenase, an enzyme known to be involved in inflammation.

Another advantage of the present invention is that the anti-inflammatory moiety and the anti-oxidant moiety are linked through an amide or ester bond. Since the carboxylic acid moiety of the NSAIA has been convened to an amide or ester, the resultant molecule is neutrally charged, thus increasing lipophilicity, and drug delivery. These compounds also associate with lipid membranes, thus providing resident antioxidant protection of these oxidizable biomolecules. Furthermore, amide or ester pro-drugs, may provide site-directed anti-inflammatory activity since amidases and esterases, components of the inflammatory response, will catalyze the hydrolysis of the amide or ester and release the non-steroidal anti-inflammatory agent and anti-oxidant.

The compounds of the present invention are capable of protecting against cellular damage by a wide range of insults. Since the compounds provide this protection by decreasing free radical or oxidative damage, reducing enzyme mediated inflammation, and improving site delivery, this therapy represents an improved two-pronged approach to the treatment of vascular inflammatory pathology.

DETAILED DESCRIPTION OF INVENTION

The compounds of the present invention are of the formula (I):

$$A-X-(CH_2)_n-Y-(CH_2)_m-Z \quad (I)$$

wherein:

A is an non-steroidal anti-inflammatory agent (NSAIA);

A—X is an ester or amide linkage derived from the carboxylic acid moiety of the NSAIA, wherein X is O or NR;

R is H, $C_1$–$C_6$ alkyl or $C_3$–$C_6$ cycloalkyl;

Y, if present, is O, NR, $C(R)_2$, CH(OH) or $S(O)_{n'}$;

n is 2 to 4 and m is 1 to 4 when Y is O, NR, or $S(O)_{n'}$;

n is 0 to 4 and m is 0 to 4 when Y is $C(R)_2$ or is not present;

n is 1 to 4 and m is 0 to 4 when Y is CH(OH);

n' is 0 to 2; and

Z is:

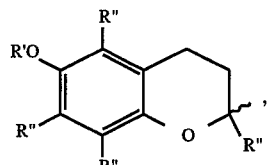

a

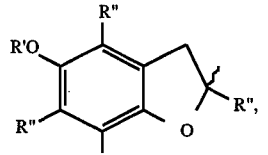

b

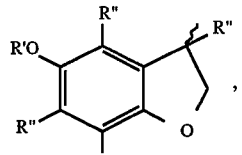

c

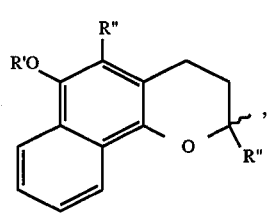

d or

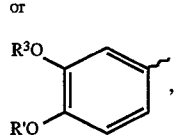

e wherein:

R' and $R^3$ are H, C(O)R, $C(O)N(R)_2$, $PO_3^-$, or $SO_3^-$;

R" is H or $C_1$–$C_6$ alkyl; and

R' and $R^3$ together may form a ring having the following structure:

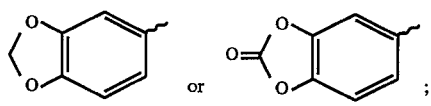

and provided that when Z is e, X is not O.

The compounds of the present invention also include pharmaceutically acceptable salts of the compounds of formula (I).

The compounds of the present invention contain a non-steroidal anti-inflammatory agent, "A", having a carboxylic moiety. A number of chemical classes of non-steroidal anti-inflammatory agents have been identified. The following text, the entire contents of which are hereby incorporated by reference in the present specification, may be referred to for various NSAIA chemical classes: *CRC Handbook of Eicosanoids: Prostaglandins, and Related Lipids, Volume II,*

*Drugs Acting Via the Eicosanoids*, pages 59–133, CRC Press, Boca Raton, Fla. (1989). The NSAIA may be selected, therefore, from a variety of chemical classes including, but not limited to, fenamic acids, such as flufenamic acid, niflumic acid and mefenamic acid; indoles, such as indomethacin, sulindac and rolmerin; phenylalkanoic acids, such as suprofen, ketorolac, flurbiprofen and ibuprofen; and phenylacetic acids, such as diclofenac. Further examples of NSAIAs are listed below:

| | | |
|---|---|---|
| pirprofen | tolfenamic acid | indoprofen |
| naproxen | clidanac | fenoprofen |
| benoxaprofen | fenclorac | meclofenamate |
| aceloferac | carprofen | isofezolac |
| fleclozic acid | fenbufen | etodolic acid |
| bromfenac | amfenac | efenamic acid |
| alcofenac | ketoprofen | fenclofenac |
| diflunisal | orpanoxin | zomopirac |
| | pranoprofen | zaltoprofen |

The preferred compounds are those wherein "A" is selected from the ester or amide derivatives of naproxen, flurbiprofen or diclofenac. The most preferred compounds are those wherein "A" is selected from the ester or amide derivatives of naproxen or flurbiprofen.

With respect to the other substituents of the compounds of formula (I), the preferred compounds are those wherein:

X is O or NR;

R is H or $C_1$–$C_3$ alkyl;

Y is CH(OH), and m is 0 to 2 and n is 1 or 2, or Y is not present, and m is 1 or 2 and n is 0 to 4;

Z is a, b, d or e;

R' and $R^3$ are H or C(O)CH$_3$; and

R" is CH$_3$.

The most preferred compounds are those wherein:

X is O or NR;

R is H;

Y is CH(OH) or is not present;

m is 0 or 1;

n is 1;

Z is a, b, d or e;

R' and $R^3$ are H; and

R" is CH$_3$.

The following compounds are particularly preferred:

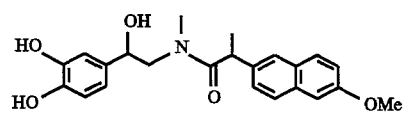

N-(2-(3,4-dihydroxyphenyl)-2-hydroxyethyl)-N-methyl 2-(6-methoxy-2-naphthyl)propionamide ("Compound A");

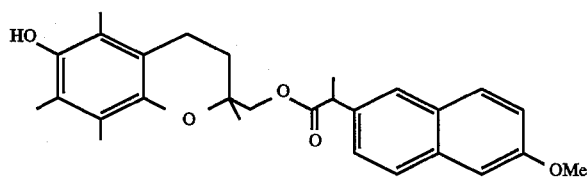

2-(6-hydroxy-2,5,7,8-tetramethyl-3,4-dihydro-2H-benzo[1,2-b]pyran-2-yl)methyl 2-(6-methoxy-2-naphthyl)propionate ("Compound B");

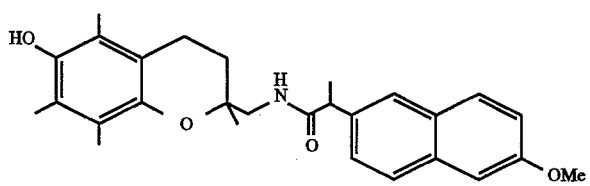

N-(2-(6-hydroxy-2,5,7,8-tetramethyl-3,4-dihydro-2H-benzo[1,2-b]pyran-2-yl)methyl) 2-(6-methoxy-2-naphthyl)propionamide ("Compound C");

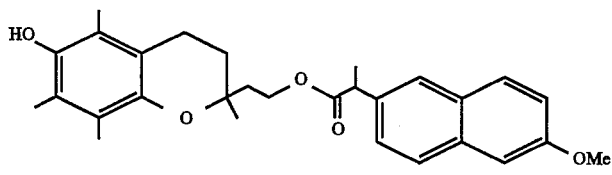

2-(6-hydroxy-2,5,7,8-tetramethyl-3,4-dihydro-2H-benzo[1,2-b]pyran-2-yl)ethyl 2-(6-methoxy-2-naphthyl)propionate ("Compound D");

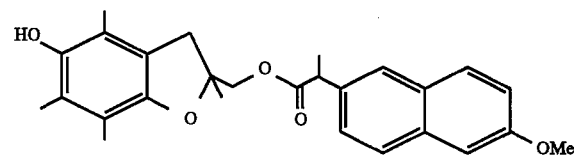

2-(5-hydroxy-2,4,6,7-tetramethyl-2,3-dihydro-benzo[1,2-b]furan-2-yl)methyl 2-(6-methoxy-2-naphthyl)propionate ("Compound E");

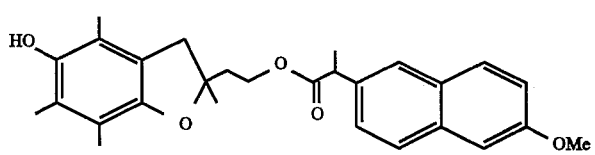

2-(5-hydroxy-2,4,6,7-tetramethyl-2,3-dihydro-benzo[1,2-b]furan-2-yl)ethyl 2-(6-methoxy-2-naphthyl)propionate ("Compound F"); and

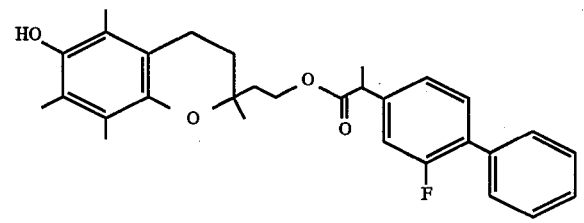

2-(6-hydroxy-2,5,7,8-tetramethyl-2,3-dihydro-2H-benzo[1,2-b]pyran-2-yl)ethyl 2-(3-fluoro-4-phenyl-phenyl)propionate ("Compound G").

The compounds of the present invention may be prepared by the methods illustrated in Scheme 1 below:

Scheme 1

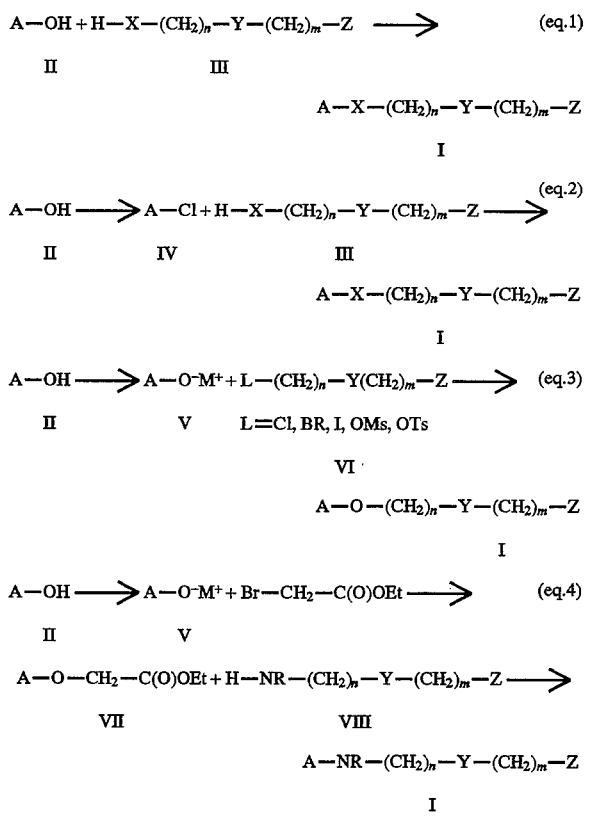

The conversion of the carboxylic acid containing nonsteroidal anti-inflammatory agents (II) to esters or amides (I) may be carried out by the following methods:

(i) As illustrated in equation 1 above, carboxylic acids (II) may be reacted with the appropriate amine or alcohol derivative (III) in the presence of a coupling reagent, such as dicyclohexylcarbodiimide or 1-(3-dimethylaminopropyl)-3-ethyl carbodiimide HCl, and 4-dimethylamine pyridine or 1-hydroxybenzotriazole, in an inert organic solvent, such as acetonitrile or tetrahydrofuran, and at a temperature from 0° C. to 50° C.

(ii) As illustrated in equation 2 above, carboxylic acids (II) may be converted to acid chlorides (IV) by reacting them with a reagent such as thionyl chloride or oxalyl chloride, in the presence of an inert solid or neat, at a temperature from 0° C. to 80° C. The resulting acid chloride (IV) may be reacted with the desired amine or alcohol (III) in an inert solvent such as tetrahydrofuran, in the presence of pyridine or a tertiary amine, such as triethylamine.

(iii) As illustrated in equation 3 above, esters (I) may be formed by reacting carboxylate anions (V), formed by reacting the carboxylic acid (II) with a base such as sodium hydride, with a halide (iodide, bromide, chloride) or sulfonate (mesylate, tosylate) (VI), in a solvent such as acetonitrile or dimethylformamide, at a temperature from 0° C. to 100° C.

(iv) As illustrated in equation 4 above, amides (I) may be prepared by reacting carboxylate anions (V), formed by reacting carboxylic acid (II) with a base such as sodium hydride, with ethyl bromoacetate. The resulting ester (VII) is reacted with the desired amine (VIII), neat or in an inert solvent, such as acetonitrile or dimethylformamide, at a temperature from 0° C. to 100° C.

The intermediate compounds (X) of Scheme 2 below, which can be used as compounds (III) and (VIII), were prepared using the general methods described in *Journal of Organic Chemistry*, volume 54, pages 3282–3292, (1989). The nitrile (IX) can be reduced using a reagent such as lithium aluminum hydride to afford the amine (X), which may be isolated as the hydrochloride salt.

The use of certain protecting groups and deprotection steps may be necessary, as will be appreciated by those skilled in the art.

Scheme 2

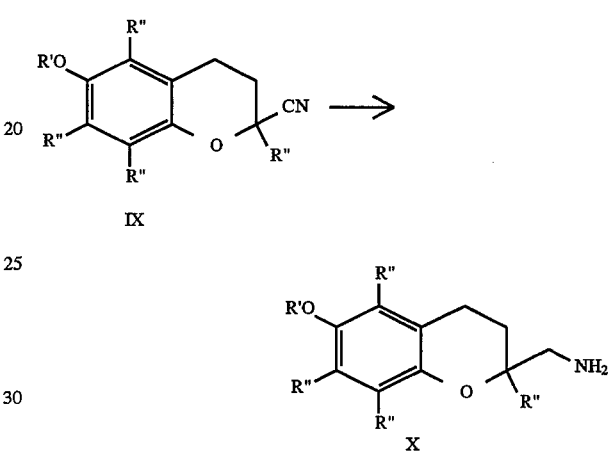

Compounds of formula (I) may exist as mixtures of stereoisomers. The preparation of the individual stereoisomers may be effected by preparing and resolving the acids (II), by known methods, and then using a single stereoisomer as starting material. Compounds (III), (VI) and (VIII) may be prepared as single stereoisomers from compounds of formula ($XI_{a-d}$), shown in Table 1 below, using known methods:

TABLE 1

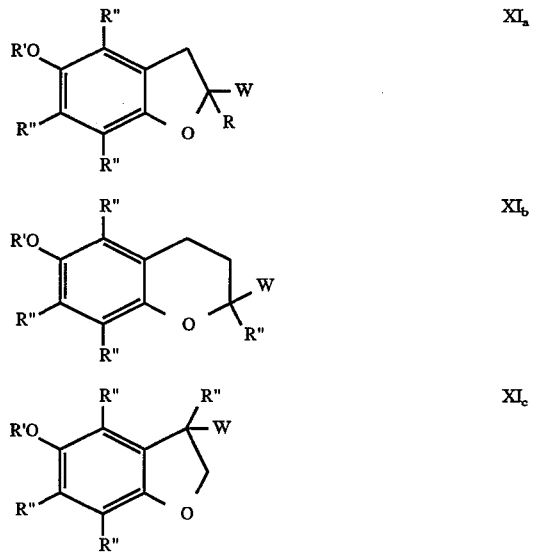

TABLE 1-continued

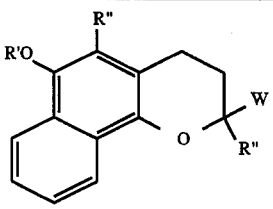

XI_d wherein:

W is (CH$_2$)$_p$—Q;
p is 0–1;
Q is CH$_2$OH or CO$_2$H;
R' is H, C(O)R, C(O)NR$_2$, PO$_3^-$, or SO$_3^-$; and
R" is H or C$_1$–C$_6$ alkyl.

The alcohols (XI$_{a-d}$) may be resolved by forming esters with optically active carboxylic acids, separating the diastereomers, and then hydrolyzing the resolved diastereomers. The corresponding carboxylic acids (XI$_{a-d}$) may be resolved by forming an ester with an optically active alcohol, separating the diastereomers, and then hydrolyzing the resolved diastereomers. Or, the carboxylic acids (XI$_{a-d}$) may be resolved by forming an amine salt with an optically active amine. Separation by recrystallization and neutralization of the resolved carboxylic acid salt may be utilized to provide the resolved carboxylic acid. Resolution of the esters and amides (I) may also be effected using chromatographic techniques known to those skilled in the art.

The amines of formula (I), where Y is NR, may be converted to amine salts by reacting the amine with acids of sufficient strength to produce an organic or inorganic salt. The pharmaceutically acceptable anions include: acetate, bromide, chloride, citrate, maleate, fumarate, mesylate, phosphate, sulfate and tartrate.

Methods of synthesizing the compounds formula (I) are further illustrated by the following examples:

EXAMPLE 1

Synthesis of N-(2(3,4-dihydroxyphenyl)-2-hydroxyethyl)-N-methyl 2-(6-methoxy-2-naphthyl)propionamide Epinephrine (Aldrich, 3.18 grams [g], 17.3 millimoles [mmol]), 1-hydroxylbenzotriazole hydrate (Aldrich, 1.76 g, 12.9 mmol) and 1-(3-dimethylaminopropyl)-3-ethyl carbodiimide HCl (Aldrich, 2.49 g, 12.9 mmol) were added to acetonitrile (200 milliliters [ml]). After stirring for 10 minutes, a solution of 6-methoxy-a-methyl-2-naphthaleneacetic acid (Aldrich, 2.0 g, 8.66 mmol), in 50 ml of acetonitrile, was added dropwise. After stirring for 16 hours, the reaction mixture was concentrated in vacuo (under reduced pressure), and the residue was partitioned between water (100 ml) and methylene chloride (100 ml). The layers were separated and the aqueous layer was extracted with methylene chloride (2×50 ml) and ethyl acetate (50 ml). The combined organic extracts were treated with methanol until a clear solution was formed. This solution was dried (magnesium sulfate) and concentrated in vacuo. Flash chromatography of the residue (silica gel, 95:5, volume:volume [v:v], methylene chloride:methanol), and concentration of the appropriate fractions resulted in the formation of a solid. The solid was recrystallized from a mixture of ethyl acetate and hexane to give N-(2(3,4-dihydroxyphenyl)-2-hydroxyethyl)-N-methyl-2-(6-methoxy-2-naphthyl)propionamide, a mixture of diastereomers, as a white solid (0.95 g, 27% yield).

$^1$H NMR (CDCl$_3$) d 1.25–1.49 (m, 3H), 2.88 (d, 3H), 3.75–4.20 (m, 2H), 3.90 (s, 3H),4.80 (m, 1H), 6.5–7.8 (m, 12H).

Elemental Analysis: Calculated for C$_{23}$H$_{25}$NO$_5$·0.5 H$_2$O Calculated for: C, 68.30; H, 6.48; N, 3.46. Found: C, 68.35; H, 6.49; H, 3.43. Melting point: 115°–117° C.

EXAMPLE 2

Synthesis of 2-(6-hydroxy-2,5,7,8-tetramethyl-3,4-dihydro-2H-benzo[1,2-b]pyran-2-yl)methyl 2-(6-methoxy-2-naphthyl)propionate A solution of 6-hydroxy-2,5,7,8-tetramethyl-2H-1-benzo[1,2-b]pyran-2-yl)methanol (2.00 g, 8.46 mmol), 6-methoxy-a-methyl naphthaleneacetic acid (2.14 g, 9.31 mmol), dimethylaminopyridine (Aldrich, 1.24 g, 10.00 mmol) and 1-(3-dimethylamino propyl)-3-ethyl-carbodiimide hydrochloride (1.71 g, 8.89 mmol), in tetrahydrofuran (40 mL), was stirred at ambient temperature under nitrogen for 72 hours. The reaction mixture was then diluted with ethyl acetate (200 mL), washed with 0.5N hydrochloride (2×250 mL), followed by water (2×250 mL), and then dried (sodium sulfate) and concentrated in vacuo. Flash chromatography of the residue (silica gel, 100–50:0–50, v:v, hexanes:ethyl acetate), and concentration of the appropriate fractions provided an oil. Crystallization from ethyl acetate-hexanes gave 2.21 g (58.3% yield) of an impure white solid. The solid was then chromatographed, and the appropriate fractions were collected and concentrated. The solid that formed was recrystallized from a mixture of ethyl acetate and hexanes to give 0.80 g (21.1% yield) of a white solid.

$^1$H-NMR(CDCl$_3$) d: 1.15 (s, 3H), 1.57–1.61 (d, 3H), 1.62–1.88 (m, 2H), 1.98–2.11 (m, 9H), 2.40–2.59 (m, 2H), 3.82–3.92 (m, 1H), 3.91 (s, 3H), 4.01–4.22 (m, 3H), 7.09–7.16 (m, 2H), 7.34–7.41 (m, 1H), 7.55–7.68 (m, 2H).

Elemental Analysis: Calculated for C$_{28}$H$_{32}$O$_5$. Calculated: C, 74.98; H, 7.19. Found: C, 75.15, H, 7.08. Melting point: 103°–105° C.

EXAMPLE 3

Synthesis of N-[(6-hydroxy-2,5,7,8-tetramethyl-3,4-dihydro-2H-1-benzo[1,2-b]pyran-2-yl)methyl]2-(6-methoxy-2-naphthyl)propionamide The intermediate, (6-hydroxy-2,5,7,8-tetramethyl-3,4-dihydro-2H-1-benzo[1,2-b]pyran-2-yl)methylamine, was first synthesized:

A 1 molar (M) ethereal solution of lithium aluminum hydride (Aldrich, 32.4 mL, 32.43 mmol) was added slowly over a 5 minute period to a chilled, (4°–6° C.) stirring solution of (2-cyano-6-hydroxy-2,5,7,8-tetramethyl-3,4-dihydro-2H-1-benzo[1,2-b]pyran in tetrahydrofuran (50 mL). After 2 hours, the reaction mixture was quenched by the slow sequential addition of 10% aqueous tetrahydrofuran (30 mL), 15% sodium hydroxide (10 mL) and then water (20 mL), while stirring. The resulting suspension was filtered through celite, and the celite pad was washed with ethyl ether (400 mL). The organic layer was separated, dried (Na$_2$SO$_4$), and concentrated in vacuo, resulting in a residue. A 1M ethereal solution of hydrochloride was then added to a solution of the residue in ethyl ether (100 mL), a solid formed, and the solid was then collected by filtration and washed with ethyl ether to give 2.31 g (65.4% yield) of a white solid. The product was used crude in the next reaction.

1H-NMR (DMSO-d$_6$/TMS): 1.15 (s, 3H), 1.75 (t, 2H), 1.99 (s, 6H), 2.01 (s, 3H), 2.54 (t, 2H), 2.98 (s, 2H).

MS (CI): 236 (m+1).

The hydrochloride salt of (6-hydroxy-2,5,7,8-tetramethyl-3,4-dihydro-2H-1-benzo[1,2-b]pyran-2-yl)methylamine (0.30 g, 1.10 mmole) and 6-methoxy-a-methyl naphthaleneacetic acid (Aldrich, 0.28 g, 1.21 mmole) were stirred in the presence of dimethylaminopyridine (Aldrich, 0.26 g, 2.20 mmole) and 1-(3-dimethylaminopropyl)-3-ethylcarbodiimide hydrochloride (Janssen Chimica-Spectrum, 0.21 g, 1.10 mmole), in tetrahydrofuran (4.0 mL) under an atmosphere of nitrogen. After stirring 17 hours at ambient temperature, the reaction mixture was diluted with ethyl acetate (70 mL), washed with water (2×15 mL), followed by brine (15 mL) and then dried (sodium sulfate). The mixture was concentrated in vacuo and the residue subjected to flash chromatography (silica gel, 100–50:0–50, v:v, hexanes:ethyl acetate). The appropriate fractions were concentrated in vacuo, and the resulting crystalline foam suspension was then washed in hexanes to give 0.28 g (58.3% yield) of N-[(5-hydroxy-2,5,7,8-tetramethyl-3,4-dihydro-2H-1-benzopyran-2-yl)methyl]-2-(6-methoxy-2-naphthyl)propionamide as a white amorphous solid.

$^1$H-NMR (CDCl$_3$) d 1.03–1.08 (d,3H), 1.57–1.64 (m, 6H), 1.70 (t, 2H,), 2.04–2.05 (m, 6H,), 2.48–2.51 (m, 2H), 3.16–3.58 (m, 2H), 3.74 (q, 1H), 3.91 (s, 3H), 4.91 (br s, 1H), 5.751 (t, 1H), 7.01–7.19 (m, 2H), 7.29–7.40 (t, 1H), 7.52–7.81 (m, 3H).

Elemental Analysis: Calculated for C$_{28}$H$_{33}$NO$_4$ Calculated: C, 75.14; H, 7.43; N, 3.13. Found: C, 75.04; H, 7.50; N, 2.97. Melting point: 67°–70° C.

EXAMPLE 4

Synthesis of 2-(6-hydroxy-2,5,7,8-tetramethyl-3,4-dihydro-2H-benzo[1,2-b]pyran-2yl)ethyl 2-(6-methoxy-2-naphthyl)propionate A solution of 1,3-dicyclohexylcarbodiimide (Aldrich, 0.89 g, 4.31 mmol) in acetonitrile (25 mL), was added dropwise to a stirring slurry of (+)-6-methoxy-a-methyl-2-naphthaleneacetic acid (Aldrich, 0.90 g, 3.91 mmol), 2-hydroxy-2,5,7,8-tetramethyl-3,4-dihydro-2H-benzo[1,2-b]pyran-2yl)ethanol (0.98 g, 3.91 mmol, U.S. Pat. No. 5,266,709 column 45) and 1-hydroxybenzotriazole hydrate (Aldrich, 0.59 g, 4.31 mmol), in acetonitrile (50 mL). After stirring for 18 hours, the reaction mixture was concentrated in vacuo. The residue was partitioned between water (30 mL) and methylene chloride (30 mL). The layers were separated, and the aqueous layer was extracted with methylene chloride (2×20 mL). The combined organic extracts were washed with water (20 mL), then dried (magnesium sulfate) and concentrated in vacuo. Flash chromatography (silica gel, 2:8, v:v, ethyl acetate:hexanes) of the residue afforded a white solid upon the concentration of the appropriate fractions. The white solid was recrystallized from an ethyl acetate-hexanes mixture to give 0.60 g (33.1% yield) of 2-(6-hydroxy-2,5,7,8-tetramethyl-3,4-dihydro-2H-benzo[1,2-b]pyran-2yl)ethyl 2-(6-methoxy-2-naphthyl)propionate, a mixture of diastereomers, as a white solid.

$^1$H NMR (CDCl$_3$) d 1.1 (d, 3H), 1.6–1.5 (m, 3H), 1.6 (m, 2H), 1.9 (m,2H). 2.0 (s, 6H), 2.1 (s, 3H), 2.4 (t, 2H), 3.8 (q, 2H), 3.9 (s, 3H), 4.2 (s, 1H), 4.1–4.4 (m, 2H), 7.1–7.7 (m,6H).

Elemental Analysis: Calculated for C$_{29}$H$_{34}$O$_5$ Calculated: C, 75.30; H, 7.41. Found: C, 75.24; H, 7.46. Melting Point: 99.5°–101.5° C.

EXAMPLE 5

Synthesis of 2-(5-hydroxy-2,4,6,7-tetramethyl-3,4-dihydro-2H-benzo[1,2-b]furan-2-yl)methyl 2-(6-methoxy-2-naphthyl)propionate A solution of (5-hydroxy-2,4,6,7-tetramethyl-2,3-dihydrobenzo[1,2-b]furan-2-yl)-methanol (0.78 g, 3.50 mmol) and 6-methoxy-a-methyl naphthaleneacetic acid (Aldrich, 0.89 g, 3.86 mmol) was stirred in the presence of dimethylaminopyridine (0.43 g, 3.51 mmol) and 1-(3-dimethylaminopropyl)-3-ethyl-carbodiimide hydrochloride (0.67 g, 3.51 mmol), in tetrahydrofuran (15 mL). The reaction mixture was stirred at ambient temperature under nitrogen for 24 hours, diluted with water (100 mL) and then washed with ethyl acetate (5×65 mL). The organic extracts were combined, and then dried (sodium sulfate) and concentrated in vacuo. The residue was subjected to flash chromatography (silica gel, 100–50:0–50, v:v, hexanes:ethyl acetate), and the appropriate fractions were combined to give 0.68 g (44.7% yield) of a foam residue. Crystallization from methylene chloride-hexanes gave 0.24 g (15.8% yield) of a pale yellow solid.

$^1$H-NMR CDCl$_3$): 1.33–1.35 (d, 3H), 1.51–1.55 (d, 3H), 1.92–1.94 (s, 3H), 2.00–2.03 (d, 3H), 2.09–2.11 (d, 3H), 2.56–2.57 (d, 1H), 2.58–2.91 (d, 1H,, 3.76–3.89 (m, 1H), 3.920 (s, 3H), 4.04–4.22 (m, 3H), 7.09–7.17 (m, 2H), 7.26–7.34 (m, 1H), 7.58–7.79 (m, 2H).

Elemental Analysis: Calculated for C$_{27}$H$_{30}$O$_5$. Calculated: C, 74.63; H, 6.96. Found: C, 74.42; H, 6.94. Melting point: 185.5°–187° C.

EXAMPLE 6

Synthesis of 2-(5-hydroxy-2,4,6,7-tetramethyl-3,4-dihydro-benzo[1,2-b]furan-2yl)ethyl 2-(6-methoxy-2-naphthyl)propionate A solution of 2-(5-hydroxy-2,4,6,7-tetramethyl-2,3-dihydrobenzo[1,2-b]furan-2-yl)ethanol (1.30 g, 5.51 mmol) and 6-methoxy-a-methyl naphthaleneacetic acid (Aldrich, 1.39 g, 6.06 mmol) was stirred in the presence of dimethylaminopyridine (0.67 g, 5.51 mmol) and 1-(3-dimethylaminopropyl)-3-ethyl-carbodiimide hydrochloride (1.06 g, 5.51 mmol), in tetrahydrofuran (25 mL). The reaction mixture was stirred at ambient temperature under nitrogen for 24 hours, diluted with ethyl acetate (150 mL), washed with water (2×40 mL) and then brine (30 mL). The organic extract was dried (sodium sulfate) and concentrated in vacuo. The residue was subjected to flash chromatography (silica gel, 100–50:0–50, v:v, hexanes:ethyl acetate), and the appropriate fractions were combined to give 1.84 g (74.5% yield) of a foam residue. Fractional crystallization and recrystallization from methylene chloride-hexanes gave 0.40 g (13.0% yield) of white solid.

$^1$H-NMR (CDCl$_3$): 1.34 (s, 3H), 1.54–1.57 (d, 3), 1.99 (t, 2H), 2.01 (s, 3H), 2.05 (s, 3H), 2.10 (s, 3), 2.73–2.81 (d, 1), 2.90–2.97 (d, 1), 3.77–3.89 (q, 1H), 3.91 (s, 3H), 4.102 (s, 1H, 4.165–4.29 (m, 2H), 7.10–7.16 (m, 2H), 7.35–7.40 (m, 1H), 7.64–7.70 (m, 2H).

Elemental Analysis: Calculated for C$_{28}$H$_{32}$O$_5$ 0.1 mole CH$_2$Cl$_2$. Calculated: C, 73.84; H, 7.10. Found: C, 73.85, 73.83; H, 7.12. Melting point: 129.5°–131° C.

EXAMPLE 7

Synthesis of 2-(6-hydroxy-2,5,7,8-tetramethyl-3,4-dihydro-2H-benzo [1,2-b]pyran-2yl)ethyl 2-(3-fluoro-4-phenyl-phenyl)propionate The intermediate, 2-(6-benzyloxy-2,5,7,8-tetramethyl-3, 4-dihydro-2H-benzo[1,2-b]pyran-2yl)ethyl 2-(3-fluoro-4-phenyl-phenyl)propionate, was first synthesized:

A solution of flurbiprofen (Sigma, 2.0 g, 8.2 mmol), 2-(6-benzyloxy-2,5,7,8-tetramethyl-3,4-dihydro-2H-benzo

[1,2-b]pyran-2-yl)ethanol (2.4 g, 8.2 mmol) 1-hydroxybenzotriazole hydrate (Aldrich, 2.4 g, 13.9 mmol) and 1-(3-dimethylaminopropyl)-3-ethyl-carbodiimide hydrochloride (Aldrich, 2.8 g, 12.3 mmol), in acetonitrile (40 ml), was stirred at ambient temperature. After 72 hours, the reaction mixture was concentrated in vacuo and the residue partitioned between water and methylene chloride. A solid formed which was removed by filtration and discarded. The layers were separated and the aqueous layer was extracted with methylene chloride (2×25 ml). The combined organic extracts were then dried (magnesium sulfate) and concentrated in vacuo. The residue was chromatographed (silica gel, 2:8, v:v, ethyl acetate:hexane). Concentration of the appropriate fractions afforded 3.0 g (64% yield, mixture of stereoisomers) of the product as a clear oil.

$^1$H NMR (CDCl$_3$) d: 1.23–1.27 (m, 3H), 1.53–1.57 (m, 3H), 1.75 (m, 2H), 1.95 (m, 2H), 2.08 (s, 3H), 2.14 (s, 3H), 2.21 (s, 3H), 2.55 (t, 3H), 3.75 (m, 2H), 4.3 (m, 1H), 4.65 (s, 2H), 7.1–7.7 (m, 13H).

A solution of 2-(6-benzyloxy-2,5,7,8-tetramethyl-3,4-dihydro-2H-benzo [1,2-b]pyran-2yl)ethyl 2-(3-fluoro-4-phenyl-phenyl)propionate in ethyl acetate was treated with 10% palladium on charcoal (Aldrich, 0.5 g). The resulting mixture was hydrogenated on a Parr Apparatus [initial pressure 60 pounds/inch$^2$ (psi)]. After 18 hours, the reaction mixture was filtered, and the resulting solution concentrated in vacuo. The residue was subjected to flash chromatography (silica gel, 2:8, v:v, ethyl acetate:hexane). Concentration of the appropriate fractions afforded a clear oil. Hexane was added to the oil and a white solid formed upon standing. The white solid was collected by filtration to afford 0.91 g (36% yield) of 2-6-ydroxy-,5,7,8-tetramethyl-,4-ihydro-H-enzo[1,2-b]pyran-yl)ethyl 2-(3-fluoro-4-phenyl-phenyl)propionate as a mixture of stereoisomers.

$^1$H NMR (CDCl$_3$) d: 1.22–1.23 (m, 3H), 1.51–1.55 (m, 3H), 1.65–1.8 (m, 2H), 1.85–2.00 (m, 2H), 2.08 (s, 6H), 2.14 (s, 3H), 2.57 (t, 2H), 3.75 (q, 1H), 4.1–4.5 (m, 2H), 7.10–7.65 (m, 8H).

Elemental Analysis: Calculated for C$_{30}$H$_{33}$FO$_4$. Calculated: C,75.60; H, 6.98. Found: C,75.69; H,7.01. Melting point: 85°–87° C.

The compounds of formula (I) may be contained in various types of pharmaceutical compositions, in accordance with formulation techniques known to those skilled in the art. For example, the compounds may be included in tablets, capsules, solutions, creams, suspensions and other dosage forms adapted for oral administration; solutions and suspensions adapted for topical or parenteral use; and suppositories for rectal use.

The present invention is particularly directed to the provision of compositions adapted for treatment of vascular tissues. The compositions of the present invention will include one or more compounds of formula (I) and a pharmaceutically acceptable vehicle for said compound(s). Various types of vehicles may be utilized. Suspensions may be preferred for compounds of formula (I) which are relatively insoluble in water.

An appropriate buffer system (e.g., sodium phosphate, sodium acetate or sodium borate) may be added to prevent pH drift under storage conditions.

Some of the compounds of formula (I) may have limited solubility in water and therefore may require a surfactant or other appropriate co-solvent in the composition. Such co-solvents include: polyethoxylated castor oils, Polysorbate 20, 60 and 80; Pluronic® F-68, F-84 and P-103 (BASF Corp., Parsippany N.J., USA); cyclodextrin; or other agents known to those skilled in the art. Such co-solvents are typically employed at a level of from 0.01 to 2 wt. %.

The pharmaceutical compositions containing one or more compound of formula (I) may be used to treat patients afflicted with or prone to various types of cellular damage. In particular, these compositions may be used for vascular inflammation where prostaglandins, leukotrienes and LDLs are known to participate. The concentrations of the compounds in the compositions will depend on various factors, including the nature of the condition to be treated with the compositions. However, the compositions may contain one or more of the compounds of the present invention in a concentration of from about 0.001 to about 5 wt. %, for topical administration.

The route of administration (e.g., topical, parenteral or oral) and the dosage regimen will be determined by skilled clinicians, based on factors such as the exact nature of the condition being treated, the severity of the condition, the age and general physical condition of the patient, and so on.

As indicated above, use of the compounds of formula (I) to prevent or reduce damage to vascular tissues at the cellular level is a particularly important aspect of the present invention. As used herein, "vascular inflammatory pathologies" refers to inflammation of the vasculature resulting from oxidation-mediated stress or stress mediated by other biochemical agents, such as cyclooxygenase or lipoxygenase inflammatory products. Vascular inflammatory pathologies which may be treated include, but are not limited to, atherosclerosis, thrombosis, hypercholesterolemia, congestive heart disease, stroke and unstable angina. The compounds may also be used as an adjunct to cardiac or brain surgery. The compounds may be used for acute treatment of temporary conditions, or may be administered chronically, especially in the case of degenerative disease. The compounds may also be used prophylactically to treat high-risk heart disease patients.

The compounds and compositions of the present invention will be used in a therapeutically effective amount. As used herein, a "therapeutically effective amount" is that amount required to prevent, reduce or ameliorate inflammation of the vasculature. The doses utilized for any of the above-described purposes will generally be from about 0.01 to about 100 milligrams per kilogram of body weight (mg/kg), administered one to four times per day.

The compounds of the present invention are further illustrated by the following in vitro and in vivo biological activity examples.

EXAMPLE 8

The antioxidant activity of representative compounds of the present invention, as compared with Vitamin E, is presented in Table 2 below. Antioxidant activity was measured using a phospholipid oxidation assay. Liposomes were formed from dilinoleolyglycerolphosphatidylcholine and the test compound. Free radical damage was induced by exposure to Fe$^{+3}$/EDTA (167 micromolar [µM]) and ascorbate (167 µM). Oxidation was terminated after one hour by freezing in liquid nitrogen. Lyophilized samples were then dissolved in methanol or water. Oxidation was measured by conjugate diene formation, monitored using UV spectroscopy as described in *Biochimica et Biophyica Acta*, volume 1081, 181–187, (1991). The IC$_{50}$ was calculated using the following non-linear regression algorithm: Y=A/[1+(B/X)$^c$], wherein A=maximum, B=IC$_{50}$ and c=cooperativity or relative broadness of the curves. The minimum was assumed to be zero.

TABLE 2

| Compound | Phospholipid Oxidation IC$_{50}$ (µM) |
|---|---|
| Compound B | 1.16 |
| Compound D | 2.23 |
| Compound E | 2.48 |
| Compound F | 2.55 |
| Vitamin E | 4.42 |

EXAMPLE 9

Inhibition of lipid peroxide formation by representative compounds of the present invention, as compared with Vitamin E, is shown in Table 3 below. The cytoprotective effects of the compounds were measured using bovine retinal pieces. Retinal tissues were incubated in hypoxic media for 1 hour. After 50 minutes of hypoxia, test agents were added to the media to allow 10 minutes for the drug to diffuse into the tissue prior to reoxygenation. The vehicle by itself, was added to the non-drug group. Following the incubation period, tissue was reoxygenated for 1 hour. Lipid peroxidation was assessed by the formation of thiobarbituric acid reacting substances (TBARS). The tissues were homogenized and added to the trichloroacetic acid-thiobarbituric acid reagent and heated in the presence of BHT. The homogenate was filtered and the absorbance of the supernant was measured spectrophotometrically. A double derivative technique was used to calculate the concentration of TBARS present in each sample. Quantitation was based on a molar extinction coefficient of $1.56 \times 10^5$.

TABLE 3

| Compound | Retinal Pieces IC$_{50}$ (µM) |
|---|---|
| Compound A | 0.15 |
| Compound D | 0.006 |
| Compound E | 0.01 |
| Vitamin E | 5.0 |

EXAMPLE 10

5-lipoxygenase inhibition by representative compounds of the present invention is shown in Table 4 below. The 5-lipoxygenase inhibitor activity was determined by measuring the inhibition of 5-HETE and LTB$_4$ formation. The ability of a compound to suppress 5-HETE and LTB$_4$ formation was investigated in calcium ionophore (A$_{23187}$)-stimulated neutrophils isolated from rabbit peripheral blood. Neutrophils were isolated by standard procedures. Briefly, heparinized/calcium chelated blood was obtained from New Zealand Albino (NZA) rabbits by heart puncture. Red cells were removed at 4° C. by dextran sedimentation, as described in *Blood*, volume 11, 436 (1956). White cells, contained in the supernatant fraction, were sedimented by centrifugation and contaminating red cells removed by hypotonic lysis. The white cell pellet obtained, following red cell lysis and centrifugation, was resuspended in Dulbecco's PBS (Ca$^{2+}$/Mg$^{2+}$-free) and layered onto a 60% Histopaque-1083®/40% Histopaque-1119® cushion (Sigma Chemical, St. Louis, Miss., U.S.A.). The Histopaque® cushion was then centrifuged, and the resulting neutrophil pellet was washed and resuspended in ¹⁄₂₅ of the original blood volume. Aliquots of the cell suspension were pretreated for 5 minutes at 37° C. with carrier (DMSO) or test article dissolved in DMSO. CaCl$_2$ was immediately added to the cell suspension and cells stimulated by addition of 5 microliters [µl] of a mixture containing [1-$^{14}$C]-arachidonic acid and A$_{23187}$ in DMSO. Final concentrations of CaCl$_2$, [1-$^{14}$C]-arachidonic acid and A$_{23187}$ were 5.0 millimolar [mM], 52 µM and 5.0 µM, respectively. After 3 minutes of incubation at 37° C., reactions were terminated by addition of 2 volumes of acetone. Extraction and reversed phase (C$_{18}$-5µ) HPLC analysis of [1-$^{14}$C]-labeled arachidonic acid metabolites are conducted as described by Graff and Anderson in *Prostaglandins*, volume 38,473 (1989).

TABLE 4

| Compound | 5-Lipoxygenase Inhibition IC$_{50}$ (µM) |
|---|---|
| Compound A | 4.0 |
| Compound D | 1.0 |

EXAMPLE 11

A respresentative compound of the present invention, Compound D, was evaluated for its ability to interact with phospholipids in monolayers and bilayers. The procedures employed to evaluate lipid interaction with lipophilic agents have been described elsewhere (*Biochemistry*, volume 34, pages 7271–7281 (1995), and Langmuir, volume 8, pages 563–570 (1992)). From these studies, it was apparent that Compound D exhibits minimal intrinsic surface-active properties. In spite of its low endogenous surface-activity, Compound D partitioned from the aqueous solution into the phospholipid monolayer at initial packing densities exceeding those believed to exist in membranes. This finding supports an energetically favorable interaction between phospholipids and representative compounds of the present invention (e.g., Compound D). Assessment of Compound D's interaction with phospholipids in a liquid-expanded monolayer state also indicated eutectic-type phase diagrams with a solubility approaching 20 to 30 mole percent in dipalmitoylphosphatidylcholine. Additional evidence for its ability to interact with phospholipids was obtained by an alteration in the fluorescence of pyrene-labeled phospholipid in a liquid-crystalline phospholipid bilayer.

What is claimed is:

1. A method of preventing or treating vascular inflammatory pathologies in a human patient which comprises administering a composition comprising a therapeutically effective amount of a compound of the following formula to the patient:

A—X—(CH$_2$)$_n$—Y—(CH$_2$)$_m$—Z wherein:

A is a non-steroidal anti-inflammatory agent originally having a carboxylic acid moiety;

X is O or NR;

A—X is an ester or amide linkage derived from the carboxylic acid moiety of the non-steroidal anti-inflammatory agent and the X;

R is H, C$_1$–C$_6$ alkyl or C$_3$–C$_6$ cycloalkyl;

Y, if present, is O, NR, C(R)$_2$, CH(OH) or S(O)$_{n'}$;

n is 2 to 4 and m is 1 to 4 when Y is O, NR, or S(O)$_{n'}$;

n is 0 to 4 and m is 0 to 4 when Y is C(R)$_2$ or is not present;

n is 1 to 4 and m is 0 to 4 when Y is CH(OH);

n' is 0 to 2; and

Z is selected from the group consisting of:

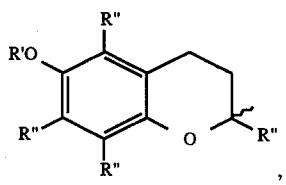

a

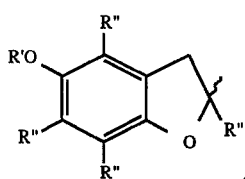

b

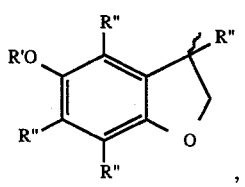

c and

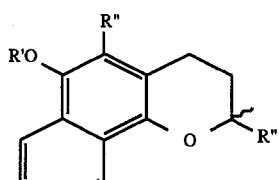

d wherein:
R' is H, C(O)R, C(O)N(R)$_2$, PO$_3^-$ or SO$_3^-$;
R" is H or C$_1$–C$_6$ alkyl;
or a pharmaceutically acceptable salt thereof; and a pharmaceutically acceptable vehicle thereof.

2. The method according to claim 1, wherein the composition is administered to prevent or treat atherosclerosis, thrombosis, hypercholesterolemia, congestive heart disease, stroke or unstable angina.

3. The method according to claim 1, wherein the composition is administered to prevent or alleviate LDL oxidation.

4. The method according to claim 1, wherein:
R is H or C$_1$–C$_3$ alkyl;
Y is CH(OH), m is 0 to 2, and n is 1 or 2, or Y is not present, m is 1 or 2, and n is 0 to 4;
Z is a, b or d;
R' is H or C(O)CH$_3$; and
R" is CH$_3$.

5. The method according to claim 1, wherein the non-steroidal anti-inflammatory agent is selected from the group consisting of: fenamic acids; indoles; and phenylalkanoic acids.

6. The method according to claim 1, wherein the non-steroidal anti-inflammatory agent is selected from the group consisting of:
loxoprofen; tolfenamic acid; indoprofen; pirprofen; clidanac; fenoprofen; naproxen; fenclorac; meclofenamate; benoxaprofen; carprofen; isofezolac; acelofenac; fenbufen; etodolic acid; fleclozic acid; amfenac; efenamic acid; bromfenac; ketoprofen; fenclofenac; alcofenac; orpanoxin; zomopirac; diflunisal; flufenamic acid; niflumic acid; mefenamic acid; pranoprofen; zaltoprofen; indomethacin; sulindac; tolmetin; suprofen; ketorolac; flurbiprofen; ibuprofen; and diclofenac.

7. The method according to claim 1, wherein the non-steroidal anti-inflammatory agent is selected from the group consisting of naproxen, flurbiprofen and diclofenac.

8. The method according to claim 1, wherein the compound is selected from the group consisting of:

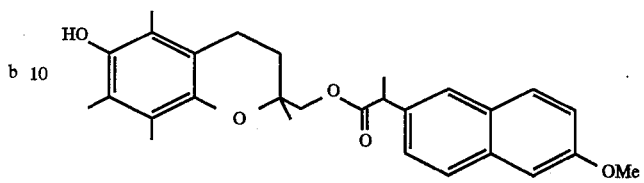

2-(6-hydroxy-2,5,7,8-tetramethyl-3,4-dihydro-2H-benzo[1,2-b]pyran-2-yl)methyl 2-(6-methoxy-2-naphthyl)propionate;

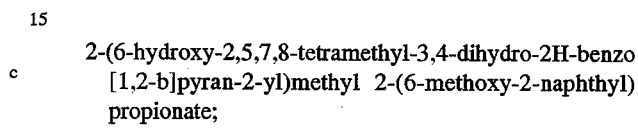

N-(2-(6-hydroxy-2,5,7,8-tetramethyl-3,4-dihydro-2H-benzo[1,2-b]pyran-2-yl)methyl) 2-(6-methoxy-2-naphthyl)propionamide;

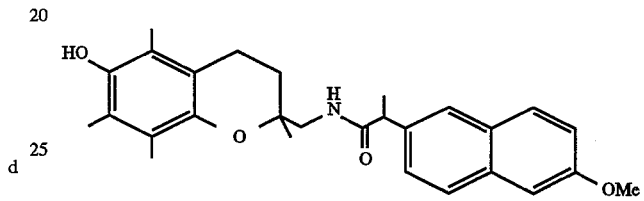

2-(6-hydroxy-2,5,7,8-tetramethyl-3,4-dihydro-2H-benzo[1,2-b]pyran-2-yl)ethyl 2-(6-methoxy-2-naphthyl)propionate;

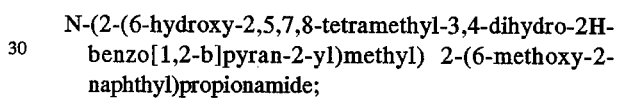

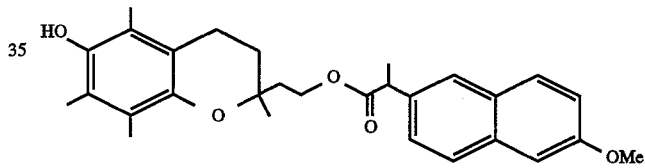

2-(5-hydroxy-2,4,6,7-tetramethyl-2,3-dihydro-benzo[1,2-b]furan-2-yl)methyl 2-(6-methoxy-2-naphthyl)propionate;

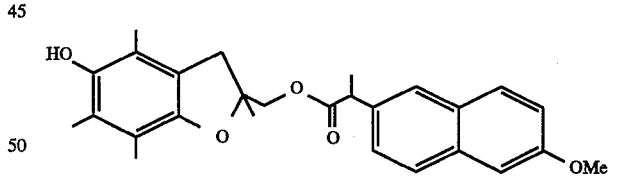

2-(5-hydroxy-2,4,6,7-tetramethyl-2,3-dihydro-benzo[1,2-b]furan-2-yl)ethyl 2-(6-methoxy-2-naphthyl)propionate; and

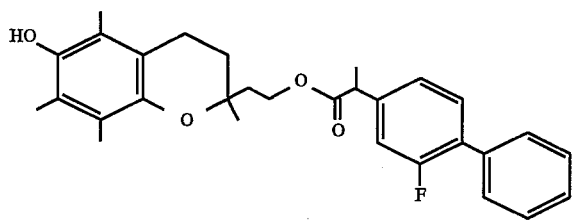

2-(6-hydroxy-2,5,7,8-tetramethyl-2,3-dihydro-2H-benzo[1,2-b]pyran-2-yl)ethyl 2-(3-fluoro-4-phenyl-phenyl)propionate.

9. A pharmaceutical composition useful in preventing or treating vascular inflammatory pathologies in a human patient which comprises administering a therapeutically effective amount of a compound of the following formula:

$$A-X-(CH_2)_n-Y-(CH_2)_m-Z$$

wherein:

A is a non-steroidal anti-inflammatory agent originally having a carboxylic acid moiety;

X is O or NR;

A—X is an ester or amide linkage derived from the carboxylic acid moiety of the non-steroidal anti-inflammatory agent and the X;

R is H, $C_1$–$C_6$ alkyl or $C_3$–$C_6$ cycloalkyl;

Y, if present, is O, NR, $C(R)_2$, CH(OH) or $S(O)_{n'}$;

n is 2 to 4 and m is 1 to 4 when Y is O, NR, or $S(O)_{n'}$;

n is 0 to 4 and m is 0 to 4 when Y is $C(R)_2$ or is not present;

n is 1 to 4 and m is 0 to 4 when Y is CH(OH);

n' is 0 to 2; and

Z is selected from the group consisting of:

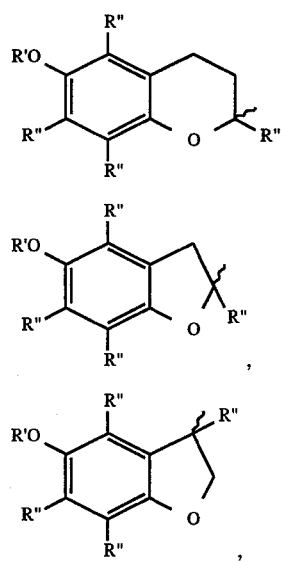

and

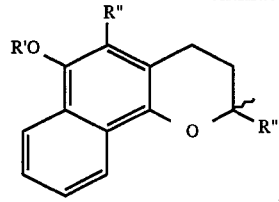

wherein:

R' is H, C(O)R, $C(O)N(R)_2$, $PO_3^-$ or $SO_3^-$;

R" is H or $C_1$–$C_6$ alkyl;

or a pharmaceutically acceptable salt thereof; and a pharmaceutically acceptable vehicle thereof.

10. The composition according to claim 9, wherein the composition is administered to prevent or treat atherosclerosis, thrombosis, hypercholesterolemia, congestive heart disease, stroke or unstable angina.

11. The composition according to claim 9, wherein the composition is administered to prevent or alleviate LDL oxidation.

12. The composition according to claim 9, wherein:

R is H or $C_1$–$C_3$ alkyl;

Y is CH(OH), m is 0 to 2, and n is 1 or 2, or Y is not present, m is 1 or 2, and n is 0 to 4;

Z is a, b or d;

R' is H, or $C(O)CH_3$; and

R" is $CH_3$.

13. The composition according to claim 9, wherein the non-steroidal anti-inflammatory agent is selected from the group consisting of: fenamic acids; indoles; and phenylalkanoic acids.

14. The composition according to claim 9, wherein the non-steroidal anti-inflammatory agent is selected from the group consisting of:

loxoprofen; tolfenamic acid; indoprofen; pirprofen; clidanac; fenoprofen; naproxen; fenclorac; meclofenamate; benoxaprofen; carprofen; isofezolac; aceclofenac; fenbufen; etodolic acid; fleclozic acid; amfenac; efenamic acid; bromfenac; ketoprofen; fenclofenac; alcofenac; orpanoxin; zomopirac; diflunisal; flufenamic acid; niflumic acid; mefenamic acid; pranoprofen; zaltoprofen; indomethacin; sulindac; tolmetin; suprofen; ketorolac; flurbiprofen; ibuprofen; and diclofenac.

15. The composition according to claim 9, wherein the non-steroidal anti-inflammatory agent is selected from the group consisting of naproxen, flurbiprofen and diclofenac.

16. The composition according to claim 9, wherein the compound is selected from the group consisting of:

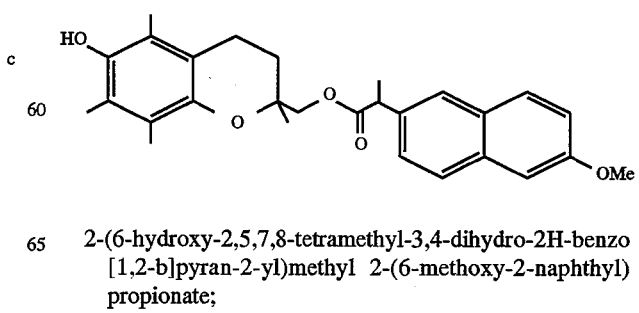

2-(6-hydroxy-2,5,7,8-tetramethyl-3,4-dihydro-2H-benzo[1,2-b]pyran-2-yl)methyl 2-(6-methoxy-2-naphthyl)propionate;

21

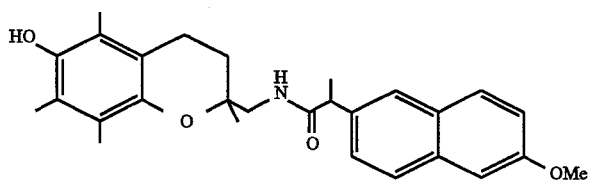

N-(2-(6-hydroxy-2,5,7,8-tetramethyl-3,4-dihydro-2H-benzo[1,2-b]pyran-2-yl)methyl) 2-(6-methoxy-2-naphthyl)propionamide;

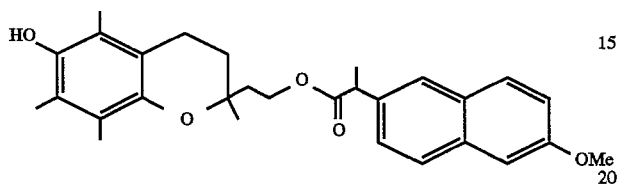

2-(6-hydroxy-2,5,7,8-tetramethyl-3,4-dihydro-2H-benzo[1,2-b]pyran-2-yl)ethyl 2-(6-methoxy-2-naphthyl)propionate;

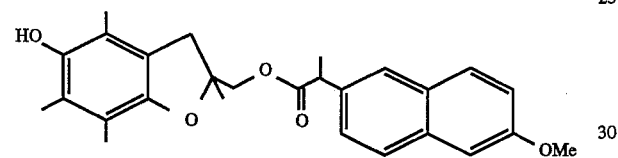

22

2-(5-hydroxy-2,4,6,7-tetramethyl-2,3-dihydro-benzo[1,2-b]furan-2-yl)methyl 2-(6-methoxy-2-naphthyl)propionate;

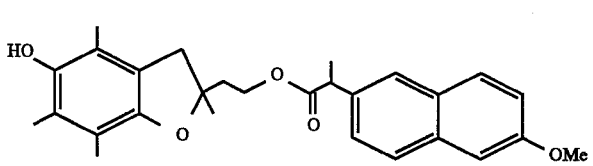

2-(5-hydroxy-2,4,6,7-tetramethyl-2,3-dihydro-benzo[1,2-b]furan-2-yl)ethyl 2-(6-methoxy-2-naphthyl)propionate; and

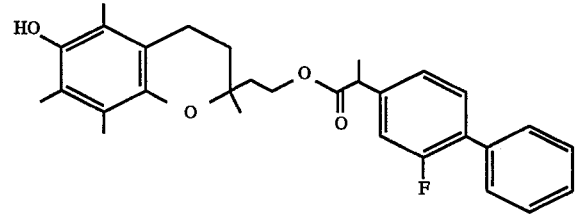

2-(6-hydroxy-2,5,7,8-tetramethyl-2,3-dihydro-2H-benzo[1,2-b]pyran-2-yl)ethyl 2-(3-fluoro-4-phenyl-phenyl)propionate.

* * * * *